United States Patent [19]

Simon

[11] Patent Number: 4,701,962
[45] Date of Patent: Oct. 27, 1987

[54] PROTECTIVE EYEWEAR

[75] Inventor: James A. Simon, Huntertown, Ind.

[73] Assignee: Eye Pro, Inc., Fort Wayne, Ind.

[21] Appl. No.: 813,070

[22] Filed: Dec. 24, 1985

[51] Int. Cl.⁴ ............................................... A61F 9/00
[52] U.S. Cl. ............................................ 2/15; 2/431; 2/439; 128/132 R
[58] Field of Search ....................... 2/15, 12, 431, 432, 2/440, 439; 128/163, 132 R

[56] References Cited

U.S. PATENT DOCUMENTS

| | | | |
|---|---|---|---|
| 2,165,668 | 7/1939 | Vaccaro | 2/15 |
| 2,283,752 | 5/1942 | Gonsett | 2/15 |
| 2,341,673 | 2/1944 | Walker | 2/431 |
| 2,572,638 | 10/1951 | Loos | 2/15 |
| 3,086,863 | 12/1962 | Bowman | 128/132 |
| 3,092,103 | 6/1963 | Mower | 2/15 |
| 3,269,267 | 8/1966 | Collins | 2/431 |
| 3,300,786 | 1/1967 | Rosenvold et al. | 128/132 R |
| 3,619,815 | 10/1969 | Towner | 2/15 |
| 3,756,692 | 9/1973 | Scott | 2/431 |
| 3,780,379 | 12/1973 | Kampman | 2/15 |
| 4,024,405 | 5/1977 | Szot | 2/15 |
| 4,122,847 | 10/1978 | Craig | 2/15 |
| 4,162,542 | 7/1979 | Frank | 2/15 |
| 4,411,263 | 10/1983 | Cook | 2/15 |
| 4,567,122 | 1/1986 | Baldry et al. | 2/432 |

Primary Examiner—Harvey C. Hornsby
Assistant Examiner—Mary A. Ellis
Attorney, Agent, or Firm—Barnes & Thornburg

[57] ABSTRACT

An adjustable, disposable eye protector is formed from an adhesive-backed ovoid to circular shaped film segment. The conical shaped eye protectors are easy to use for reducing exposure of the eyes to incident light or other potential eye irritants. When formed from polymeric film segments having low ultraviolet (UV) transmittance, the present eye protectors are used effectively to protect eyes from harmful UV radiation.

7 Claims, 9 Drawing Figures

PROTECTIVE EYEWEAR

BACKGROUND AND SUMMARY OF THE INVENTION

This invention relates to disposable protective eyewear. More particularly, the present invention is directed to adjustable eye protectors intended for one-time use to reduce the exposure of eyes to incident light and other potential eye irritants.

The human eye is a sensitive organ. Because of its sensitivity and its constant exposure to the environment during every person's routine daily activities, the eye is perhaps more susceptible to irritation and injury than any other human organ. We are reminded constantly of the importance of eye safety and protection from the possible causes of eye injury, namely damaging radiation, projectiles and potential eye irritants. Warnings to use appropriate eye protection measures appear on everything from hammers to hair colorings.

Intense visible light or radiation of shorter wavelength, i.e., between about 200 and about 400 nanometers (ultraviolet radiation), from the sun or from artificial light sources poses a significant risk of eye damage. The eye is particularly susceptible to damage from exposure to ultraviolet radiation because the damaging radiation cannot itself be sensed by the light receptors in the eye. In other words, ultraviolet (UV) radiation is invisible to the eye, and the injury is not apparent until after the damage is done. While the UV radiation component of sunlight can itself damage the eyes without proper precaution, the majority of cases of UV radiation eye damage has resulted from the use, or more appropriately the misuse, of artificial sunlamp products in the home or in commercial tanning salons. Responsive to that fact, federal regulations have been promulgated to specify safety standards for the manufacture and use of UV emitting products. One of those regulations (21 C.F.R. § 1040.20) requires that protective eyewear be provided and used with all UV emitting lamps. To comply with these regulations some lamp manufacturers and many tanning salon proprietors have been supplying customers with reusable goggle-type protective eyewear, which although functional to protect the eyes, are uncomfortable and not size-adjustable to fit each prospective user. Moreover, reusable protective eyewear preesnts certain sanitary problems—they can serve as a means for spreading communicable eye diseases of both microbial and viral origin. This fact, especially with the present day fear of contracting certain viral infections, prompts many users of UV light emitting products to refuse to use appropriate protective eyewear. Reusable goggles, although available to the customer, are often simply not used.

Clearly the availability of a disposable, adjustable, and inexpensive eye protector for use with UV emitting devices and for use in other circumstances requiring temporary protection of the eye from potential eye irritants, would meet important public health and safety needs. Not only would such promote the use of appropriate eye protection at home and in the increasingly popular tanning salons, but it would also help to minimize the spread of disease possibly associated with reusable protective eyewear.

Disposable eye protectors are not new. Several early inventors faced with the need for easy to use eye protectors developed and patented occular patch-type protective eyewear in both disposable and reusable forms. See, for example, the eye protectors or eye shields disclosed in U.S. Pat. Nos. 2,165,668; 2,283,752; 2,572,638; 3,068,863; and 2,527,947. While the patch-type eye protectors disclosed in those early patents, as well as other more recently developed forms of protective eyewear, do function to protect the eyes from potential eye irritants and harmful radiation, none of them were designed (1) to be adjustable to maximize user fit and comfort; (2) to selectively transmit at least a portion of visible light so that the user can "see" while wearing the protective eyewear; or (3) to be shaped to conform to the facial tissue adjacent the eye and to allow for substantially unhindered eye lid movement when the eye protector is positioned over the eye.

Accordingly, it is an object of the present invention to provide an inexpensive, disposable eye protector.

Another object of the present invention is to provide a method for reducing exposure of an eye to eye irritants and to potentially harmful light radiation by forming a film segment having an applied contact adhesive into a contoured cone-shaped eye protector and positioning said eye protector to cover the eye.

A further object of the present invention is to provide simple but functional protective eyewear adapted to be size-adjustable for a conforming fit.

Still another object of this invention is to provide an adjustable, disposble eye protector which reduces the exposure of an eye to harmful irritants and UV radiation while at the same time allowing sufficient transmission of visible light to allow the user to see.

It is still a further object of the present invention to provide an eye protector formed from a slotted ovoid to circular shaped segment of UV light absorbing film having an applied contact adhesive.

Another object of this invention is to provide a method of protecting an eye by covering the eye with an eye protector formed from a circular to ovoid shaped film segment, having a locus of applied contact adhesive, into a size-adjustable, cone-shaped protective device having a base marginally shaped as to be conformable to the facial contours continguous to the eyes; the contact adhesive applied to the film segment functions both as a shape-retaining means for the cone-shaped eye protector and as a position-retaining means when the protector is positioned to cover the eye.

Those and other objects of this invention will be apparent from the following detailed description of the invention as illustrated by way of example in the accompanying drawings.

SUMMARY OF THE INVENTION

Figure 1:
FIG. 1 is a perspective view illustrating one of the present eye protectors in use.

This invention is directed to an adjustable, disposable eye protector and to a method of using that eye protector, among others, for reducing the exposure of an eye to potential eye irritants and to incident radiation selected from ultraviolet, visible and infrared light. As shown in FIG. 1, in accordance with this invention, eye protector 10 is formed into a conical shape and is then located over the eye in an adhesively retained position. In practice, a pair of protectors are used, each one positioned to cover an eye. The present eye protectors are formed from adhesive bearing, ovoid to circular shaped (preferably oval shaped) film segments comprising a polymeric film having a radiation transmittance value of less than 1 for at least a portion of incident ultraviolet, visible or infrared radiation.

DETAILED DESCRIPTION OF THE INVENTION

Referring to the drawings, in accordance with the method of the present invention a contact adhesive is applied to a locus 12 on a first side 14 (ultimately the eye proximal concave side of the formed conical eye protector 10) of an ovoid to circular shaped film segment 16. The locus 12 of applied adhesive is coincident with at least a portion of a peripheral edge 18 of the shaped film segment 16. Preferably the locus 12 of the contact adhesive is coincident with greater that about 20 percent of the arcuate length of peripheral edge 18 of shaped segment 16, and does not include the surface of the shaped segment which will be in contact with the user's eyelashes when the formed eye protector 10 is positioned to cover the eye. Thus the adhesive is preferably not applied to areas on the surface of the film segment other than those proximal to the peripheral edge 18. Illustrative of preferred locii 12 of contact adhesive on the side 14 of the shaped film segment 16 are illustrated particularly in FIGS. 2, 4 and 7-9.

The nature of the contact adhesive utilized in accordance with the present invention is not critical. Many synthetic acrylic and natural rubber-based contact adhesives are known in the art. Preferably, the contact adhesive is a non-allergenic, medical grade adhesive such as those which have been used on medical tapes and dressings. Such contact adhesives are commercially available, for example, in the form of a transfer tape with a release liner. Thus, in practice the shaped film segment 16 can be cut from a sheet of polymeric film or film laminate, hereinafter described, on which a transfer tape has been applied in a predetermined pattern so that the die cut film segments 16 each have the desired locus 12 of applied contact adhesive. Where the contact adhesive is applied via transfer tape with a release liner, a preferred embodiment of the present invention, the adhesive is exposed on the film segment 16 by removal of the release liner before the cone-shaped eye protector 10 is formed from film segment 16 and applied to cover the eye.

The ovoid to circular shaped, preferably oval shaped, film segment 16 having a locus 12 of applied adhesive is formed into a substantially cone-shaped eye protector 10 so that the peripheral edge 18 of the segment essentially forms the base 20 of the eye protector 10. FIGS. 3 and 5 illustrate formation of the cone-shaped eye protector 10 from the adhesive-bearing shaped film segments 16 illustrated in FIGS. 2 and 4, respectively. The shaped film segment 16 can be folded along phantom lines a, b, and c (FIG. 2) to bring adjacent surfaces in the adhesive locus 12 near the peripheral edge 18 of the segment in adhesive contact to form the substantially cone-shaped eye protector 10 shown in FIG. 3 having an adhesively retained fold 15 on eye distal (convex) second side 22 of the eye protector 10. Fold 15 can serve as a gripping means for the formed cone-shaped eye protector. At least a portion of the adhesive locus 12 is exposed on the eye proximal (concave) first side 14 of the eye protector 10 near base 20 (corresponding to the peripheral edge 18 of film segment 16). The exposed adhesive locus functions as a position retaining means when eye protector 10 is positioned to cover the eye. It forms adhesive contact with the fleshy structures in the eye cavity.

Figure 4:
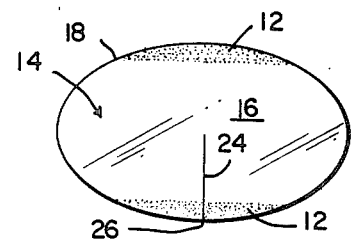
FIG. 4 is a plan view of a preferred film segment used to form an eye protector in accordance with the present invention.
Figure 7:
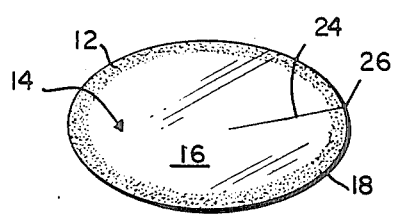
FIGS. 7-9 are each plan views of film material of different shapes from which the eye protectors in accordance with this invention can be formed.
Figure 5:
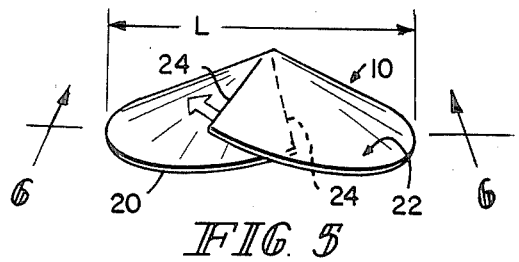
FIG. 5 is a top perspective view of a cone-shaped eye protector formed from the film segment shown in FIG. 4.
Figure 8:
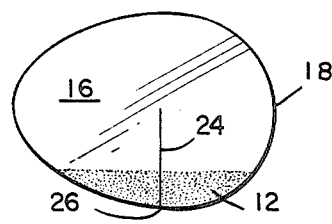

In a preferred embodiment of the present invention illustrated in FIG. 4, shaped film segment 16 has a scission line 24 extending radially inward from a point 26 on the peripheral edge 18 toward the center of the segment. The locus 12 of the applied adhesive is coincident with at least a portion of the radially inwardly extending scission line 24 and the peripheral edge 18. Again, it is preferred that the locus 12 of applied adhesive be coincident with at least about 20 percent of the arcuate length of the peripheral edge 18 of the film segment 16. In this preferred embodiment of the present invention, film segment 16 is formed into a substantially cone-shaped eye protector 10 by overlapping the edges of the scission line 24 to adhesively engage those overlapped edges so that the peripheral edge 18 of the segment essentially forms the base 20 of cone-shaped eye protector 10.

Figure 2:
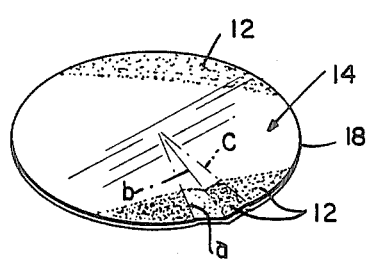
FIG. 2 is a plan view of a film segment used to form one of the present eye protectors.
Figure 3:
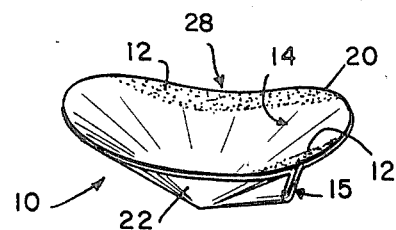
FIG. 3 is a perspective view of a cone-shaped eye protector formed by folding the film segment shown in FIG. 3.

Whether the cone-shaped eye protector is formed by the folding embodiment illustrated in FIGS. 2-3 or the scission-line-overlapping procedure illustrated in FIGS. 4-5, the size of the cone-shaped eye protector, and to some extent the conformation of the base 20, can be adjusted by the size of the fold 15 or the amount of overlap, respectively. Thus, the distance L in FIG. 3 can be reduces, for example, by increasing the amount of overlap of the sides of the scission line 24.

The composition of the film segment itself is not critical to the present invention so long as its spectral transmittance and other physical properties are such that it will afford the desired eye protection. For example, if in accordance with the present method, the eye protector is intended to protect the eye against eye irritants such as those which may be encountered in certain hair treatments, the film segment should be liquid impervious. Also at one extreme the segment could be totally opaque, and at the other extreme, substantially transparent. Since most users of protective eyewear prefer to "see" while the protective eyewear is in place covering the eyes, it is preferred in accordance with this invention to form the film segment from a polymeric film which is transparent to at least a portion of incident visible radiation.

Where the protective eyewear in accordance with this invention is used to reduce the exposure of an eye to ultraviolet radiation, the shaped film segment should be formed from a film comprising an ultraviolet light absorbing polymer. Ideally the film segment should be essentially opaque to ultraviolet light. Federal regulations specify that protective eyewear for use with UV emitting sunlamp products have a radiation transmittance of less than about 0.001 for radiation having a wavelength ranging from about 200 to about 320 nanometers and a transmittance value less than about 0.01 for radiation having a wavelength ranging from about 320 nanometers to about 360 nanometers.

Polymeric films suitable for use in accordance with the present invention are well known in the art and readily available commercially either as monolayer films or multilayer film laminates. Thus, the shaped film segment 16 in accordance with the present invention can be formed from a monolayer or multilayer laminate of a polymeric film selected from acrylic polymers, for example, acrylate, methacrylate and copolymers thereof; polyethylene and copolymers and ethylene and other olefin monomers such as hexene-1 and butene-1; polypropylene; polyvinylchloride and copolymers thereof; nylon; and polyesters, for example, polyethylene terephthalate. Such polymeric films are well known in the art and are commercially available in thicknesses ranging from less than 0.5 mils to more than 10 mils (1 mil equals 0.001 inch).

The optical properties, and other physical properties, of an eye protector in accordance with the present invention is determined by the thickness and composition of the polymeric material(s) used for forming the film segment 16. For example, light transmittance of the film segment, and therefore that of the eye protector, can be reduced by utilizing a vacuum metallized polymeric film, usually a biaxially oriented polymeric film, to form the shaped film segment. In a preferred embodiment of this invention the film segment 16 is formed from a laminate of two or more polymeric films, at least one of which is a metallized biaxially oriented polyethyleneterephthalate. Such metallized film laminates are well known in the art and have found utility as solar control film and as packaging material for various foods. The second polymeric film layer in such art-recognized laminates is typically a polyester or a polyolefin such as polyethylene.

In a preferred embodiment of the present invention the eye protector is formed from a film segment having reduced transmittance of ultraviolet (UV) radiation. Some polymers, for example those containing aromatic ring structures and other UV absorbing functional groups, strongly absorb UV radiation and inherently have low UV transmittance. Other types of polymeric films not inherently having such UV absorbing polymeric groups can be modified by including art-recognized UV absorbing "stabilizers" during the polymer film formation process.

Commonly used UV stabilizing compounds are substituted benzophenone and substituted benzotriazole compounds. The most common benzophenone compounds used as UV stabilizers for polymeric films are 2,4-dihydroxy-benzophenone, 2-hydroxy-4-acryloxyethoxy-benzophenone, 2-hydroxy-4-methoxy-benzophenone, 2,2'-dihydroxy-4-methoxy-benzophenone, 2,2'-dihydroxy-4,4'-dimethoxy-benzophenone, 2-hydroxy-4-n-octoxy-benzophenone, 2,2',4,4'-tetrahydroxy-benzophenone, and 4-dodecyloxy-2-hydroxy-benzophenone. Most common of the substituted benzotriazoles used as UV stabilizers in polymeric films are 2(2'-hydroxy-5'-methylphenyl) benzotriazole, 2-(3,3',5'-di-t-butyl-2'-hydroxyphenyl)-5-chlorobenzotriazole, 2-(3'-t-butyl-2'-hydroxy-5'-methylphenyl)-5-chlorobenzotriazole, 2(2'-hydroxy-3',5'-di-t-butylphenyl)benzotriazole, 2(2'-hydroxy-3',5'-di-t-amylphenyl)benzotriazole, and 2-(2'-hydroxy-5-t-octylphenyl)benzotriazole. Addition of such UV stabilizers to polymeric films not only reduces UV light-induced degradation of those films in the long term, but also reduces film transmittance of UV light. Polymeric films formulated using such ultraviolet stabilizers are well known in the art, as are laminates of such UV stabilized film with, for example, metallized biaxially oriented polymeric film.

Transmittance properties of film laminates can also be controlled to some extent by the nature and components of the laminating adhesive used to adhere the component films forming the film laminate. Thus, UV absorbance of a film segment in accordance with this invention can be minimized by forming the segment from a film laminate using polymeric films (1) which inherently have UV absorbing functional groups, (2) which have been UV stabilized by the use of art-recognized UV stabilizers and (3) which have been laminated using adhesives comprising compounds having UV absorbing functional groups.

In a preferred embodiment the film segment has a transmittance value of less than about 0.001 for radiation having a wavelength from about 200 to about 320 nanometers and a transmittance value of less than about 0.01 for radiation having a wavelength ranging from about 320 to about 360 nanometers while at the same time being transparent to at least a portion of incident visible radiation. In a most preferred embodiment of the present invention the shaped film segment is formed from a partially transparent film laminate comprising a biaxially oriented metallized polyethyleneterephthalate film and a medium to low density UV stabilized polyethylene or polyester film. Preferably the thickness of the film laminate is between about 2 mils and about 8 mils.

Figure 6:
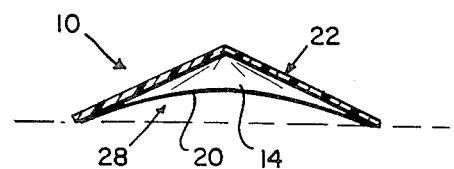
FIG. 6 is a cross-sectional view of the cone-shaped eye protector shown in FIG. 5 taken at line 6—6.
Figure 9:
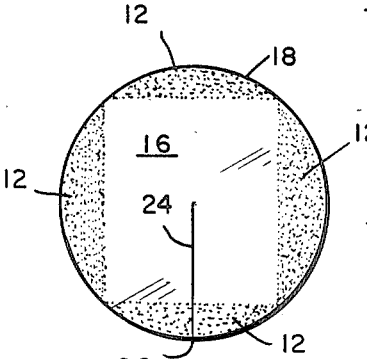

When a non-circular shaped film segment 16 is formed into a substantially cone-shaped eye protector in accordance with the present invention, the base 20 of the cone-shaped eye protector, viewed cross-sectionally, as illustrated in FIG. 6, assumes an arch-like configuration 28 which conforms to the contours of the flesh immediately adjacent to the eye in the eye cavity. This advantageously allows for a good fit of the eye protector against the skin surrounding the eye when the eye protector is positioned to cover the eye. Moreover the conical shape of the eye protector allows space for eyelid movement even when the protector is positioned in an adhesively retained position over the eye. This is important in applications of the eye protector where the user needs to have at least some ability to "see" while the eye protector is in place.

Once the user discontinues the activity requiring eye protection or otherwise determines that eye protection is no longer required, the protective eyewear in accordance with the present invention can be easily removed from their location over the eyes by carefully peeling them from their adhesively retained positions. While the present eye protectors are designed to be disposable after use, their reuse is possible, but limited by the decreased effectiveness of the contact adhesive after first-time use.

The present invention has been described in conjunction with the preferred embodiments. Those skilled in the art will appreciate that many modificatons and changes may be made to the preferred embodiments without departing from the present invention. It is therefore not intended to limit the present invention except as set forth in the appended claims.

I claim:

1. A method for reducing the exposure of an eye to eye irritants and to incident radiation selected from ultraviolet, visible and infrared light, which method comprises forming an ovoid to circular shaped film segment, said segment comprising a polymeric film having a radiation transmittance value of less than 1 for at least a portion of said incident radiation, applying a contact adhesive to a locus on one side of the shaped film segment, said locus being coincident with at least a portion of a peripheral edge of the shaped film segment, forming said segment into a substantially cone-shaped eye protector so that the peripheral edge of the segment essentially forms the base of the cone-shaped eye protector, and positioning said eye protector to cover the eye so that the base of the cone-shaped eye protector is in adhesive contact with the fleshy structures immediately adjacent the eye in the eye cavity, in which method the adhesive applied on one side of the shaped film segment functions both as a shape retaining means for the eye protector and as a position retaining means when the eye protector is positioned to cover the eye.

2. The method of claim 1 wherein the shaped segment has a radially extending scission line traversing the locus of adhesive and extending from a point on its peripheral edge toward the center of the segment, and the segment is formed into the substantially cone-shaped eye protector by overlapping the edges of the radially extending scission line to adhesively engage said overlapped edges.

3. The method of claim 1 wherein the substantially cone-shaped eye protector is formed from the shaped film segment by folding said segment to bring adjacent surfaces in the adhesive locus near the peripheral edge of the segment in cone-forming adhesive contact.

4. The method of claim 2 wherein the film segment is a layered polymeric film laminate.

5. The method of claim 4 wherein at least one layer of the polymeric film laminate is a biaxially oriented metallized polymeric film.

6. The method of claim 5 wherein the polymeric film laminate further comprises a UV stabilised polymeric film.

7. The method of claim 5 wherein the eye protector has a radiation transmittance value of less than 0.001 for radiation having a wavelength ranging from about 200 to about 320 nanometers and a value less than about 0.01 of radiation having a wavelength ranging from about 320 nanometers through about 360 nanometers and wherein the eye protector is transparent to at least a portion of incident visible radiation.

* * * * *

UNITED STATES PATENT AND TRADEMARK OFFICE
CERTIFICATE OF CORRECTION

PATENT NO. : 4,701,962

DATED : October 27, 1987

INVENTOR(S) : James A. Simon

It is certified that error appears in the above-identified patent and that said Letters Patent is hereby corrected as shown below:

In column 1, line 47, replace "preesnts" with -- presents --.

In column 3, line 32, replace "that" with -- than --.

In column 4, line 43, replace "reduces" with -- reduced --.

In column 5, line 14, replace "and" (second occurrence) with -- of --.

In column 6, line 63, replace "modificatons" with -- modifications --.

Signed and Sealed this

Nineteenth Day of April, 1988

Attest:

DONALD J. QUIGG

*Attesting Officer*   *Commissioner of Patents and Trademarks*